United States Patent
Simpson

(10) Patent No.: US 6,420,332 B1
(45) Date of Patent: Jul. 16, 2002

(54) BLOOD AND ORGANIC STAIN REMOVER

(76) Inventor: Joseph J. Simpson, 120 Commandants Way, Chelsea, MA (US) 02150

(*) Notice: Subject to any disclaimer, the term of this patent is extended or adjusted under 35 U.S.C. 154(b) by 0 days.

(21) Appl. No.: 09/469,602

(22) Filed: Dec. 21, 1999

Related U.S. Application Data

(60) Provisional application No. 60/113,830, filed on Dec. 23, 1998.

(51) Int. Cl.[7] .......................... C11D 3/386; C11D 1/83; C11D 7/42; C11D 17/00; A47L 13/16

(52) U.S. Cl. .................. 510/439; 510/300; 510/306; 510/320; 510/342; 510/356; 510/363; 510/393; 510/530; 510/438; 15/209.1

(58) Field of Search ...................... 510/300, 306, 510/320, 342, 356, 363, 393, 530, 438, 439; 15/209.1

(56) References Cited

U.S. PATENT DOCUMENTS

| | | | |
|---|---|---|---|
| 3,819,528 A | 6/1974 | Berry | 252/153 |
| 4,243,546 A | 1/1981 | Shaer | 252/174.12 |
| 4,287,082 A | 9/1981 | Tolfo et al. | 252/174.12 |
| 4,305,837 A | 12/1981 | Kaminsky et al. | 252/174.12 |
| 4,537,707 A * | 8/1985 | Severson, Jr. | 252/545 |
| 4,561,991 A * | 12/1985 | Herbots et al. | 252/118 |
| 4,998,984 A * | 3/1991 | McClendon | 206/205 |
| 5,030,378 A * | 7/1991 | Venegas | 252/174.12 |
| 5,422,030 A * | 6/1995 | Panandiker et al. | 252/135 |
| 5,501,820 A | 3/1996 | van den Bergh et al. | 252/549 |
| 5,773,405 A | 6/1998 | Bruhnke | 510/519 |
| 5,851,973 A | 12/1998 | Foley | 510/235 |
| 5,990,065 A * | 11/1999 | Vinson et al. | 510/237 |
| 6,013,614 A * | 1/2000 | Mahdessian | 510/277 |

FOREIGN PATENT DOCUMENTS

| | | | |
|---|---|---|---|
| EP | 0611206 | | 8/1994 |
| EP | WO 98/28392 | * | 7/1998 |

* cited by examiner

Primary Examiner—Yogendra N. Gupta
Assistant Examiner—Brian P. Mruk
(74) Attorney, Agent, or Firm—Perkins, Smith & Cohen, LLP; Jerry Cohen; Jacob N. Erlich

(57) ABSTRACT

The present invention is a blood and organic stain remover which includes in a first embodiment a protease, an amylase, an enzyme stabilizing system such as a source of calcium, an alcohol, and an alkanolamine, a nonionic detergent, and water. In a second embodiment, the blood and organic stain remover includes a protease, an amylase, an enzyme stabilizing system, a nonionic detergent, an anionic detergent, and water. In the second embodiment the enzyme stabilizing system preferably includes a petroleum distillate. A system of using the aqueous blood and organic stain remover composition in a prepackaged wipe which permits the user to remove blood and organic spots or to pre-spot blood and organic stains prior to washing without the need for direct skin contact with the spot is also provided.

27 Claims, 4 Drawing Sheets

BLOOD AND ORGANIC STAIN REMOVER

CROSS REFERENCE TO RELATED APPLICATIONS

This Application claims priority from the Provisional Application Ser. No. 60/113,830 entitled, "A Blood and Organic Stain Remover," filed on Dec. 23, 1998.

FIELD OF THE INVENTION

The instant invention relates to the field of spot and stain removers for removing blood and organic stains. These blood and organic stain remover compositions contain at least two different types of enzymes and are stable with time as evidenced by sustained enzyme activity. The inventive spot and stain removers find use in medical offices, hospitals, and the like.

BACKGROUND OF THE INVENTION

Blood and other organic stains such as for example urine, feces, vomit and the like, are notoriously difficult to remove from fabrics, such as for example clothing, and from hard surfaces, such as for example hardwood floors, cabinet counters, and dental instruments. Pre-spotting prior to the laundering of a garment is typically attempted using a liquid pre-spotting formulation or semi-solid stick formulation containing a detergent.

Pre-spotting with a detergent formulation alone has been at best only moderately successful at removing organic stains. Addition of an enzyme that is a protease can potentially digest or at least partially digest the protein in the blood or organic stain. However, enzyme containing liquid spot removers have known problems. Separation of the different components of an aqueous spot remover containing an enzyme(s) into different layers or phases (termed phase separation) and a resulting decrease in spot removing capacity is known to occur.

Additionally, since enzymes themselves are proteins, they can digest each other. Further, enzymes must maintain a certain chemical configuration or shape in order to remain active. A change to that configuration which results in inactivation is called denaturation. Heat, unfavorable pH, and other such conditions may result in denaturation or partial denaturation of the enzyme, thus decreasing the shelf-life of the spot remover or at least rendering the spot remover less effective with time. Formulating an effective organic spot remover containing enzymes that remains phase stable and that maintains enzymatic activity has proven difficult. Further, many spot removers contain phosphates and other chemicals that can pollute the environment.

Various patents have proposed ways to stabilize single enzyme type detergent compositions. U.S. Pat. No. 3,819,528 provides an aqueous enzyme composition wherein the enzyme is an amylase. A water soluble calcium salt, and an organic stabilizing agent such as 1,3-propanediol or an aliphatic glycol are illustrated as stabilizers. U.S. Pat. No. 4,287,082 (Tolfo, et al.), incorporated herein by reference, discloses a homogeneous proteolytic enzyme-containing liquid detergent composition containing saturatured fatty acids. U.S. Pat. No. 5,422,030, the disclosure of which is incorporated herein by reference, provides liquid detergents with an aromatic borate ester to inhibit proteolytic enzyme degradation of the enzymes in the composition.

SUMMARY OF THE INVENTION

It is an object of the instant invention to provide a liquid spot or pre-spot remover solution containing detergent and at least two enzymes that has enhanced enzymatic stability and sustained organic and blood spot removing capacity.

It is an additional object to provide a blood and organic spot remover that is environmentally friendly and that is biodegradable.

It is a further object of the instant invention to provide a liquid spot or pre-spot remover containing detergent and at least one protease enzyme where the activity of the protease enzyme is at least 80%, and preferably 90% or greater, for at least eight weeks.

It is a still further object of the instant invention to provide a spot or pre-spot remover having an enzyme system comprising at least two enzymes, a protease and an alpha amylase and a detergent that maintains activity or enzymatic stability for at least eight weeks. Enzymatic stability is defined as the ability of an enzyme to maintain its catalytic activity to a designated substrate in order to digest the substrate into shortened components that are more easily washed away in detergent and/or with water. Preferably the spot remover composition as a whole is phase stable and active for at least eight weeks.

It is an additional object of the present invention to provide a blood and organic spot remover that has germicidal activity.

The instant invention is a blood and organic stain remover comprising a protease, an amylase, an enzyme stabilizing system, a nonionic detergent, and water. A method of using the aqueous blood and organic stain remover composition as a germicide is also provided. The composition may be incorporated into a pre-moistened prepackaged wiper that allows the user to remove a blood and organic stain without coming into direct contact with the stain. The packaging folds so that the moistened area of the wiper need not come in contact with the skin of the user. The wiper is especially useful for cleaning clothing and hard surfaces such as for example, tables, chairs, instruments and the like.

DETAILED DESCRIPTION OF THE INVENTION

Figure 1:
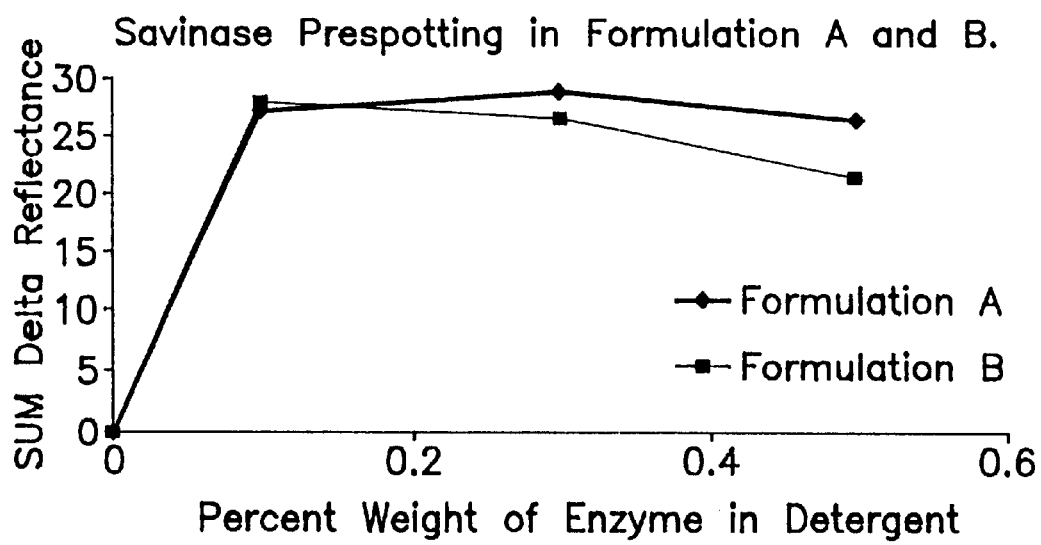
FIG. 1 illustrates the ability of Formula A and Formula B to remove stains containing protein therein as measured by reflectance.

In accordance with the present invention, it has been found that by combining a nonionic surfactant or a mixture of nonionic and anionic surfactants, a protease or a mixture of a protease and an amylase, and a stabilizing system, effective organic spot removing enzymatic activity in an aqueous detergent solution may be maintained for prolonged periods of time.

In the inventive organic stain remover, water comprises up to 50% by weight of the total composition. The amount of water present will vary depending upon the other solvents needed to dissolve certain components of the formulation(s)

and/or to clarify the liquid composition. The preferred amount of water is from about 40% to about 60%.

Organic Synthetic Surface-Active Agents:

The preferred organic synthetic surface-active agents are biodegradable and are nonionic surfactants, anioinic surfactants, or mixtures of nonionic and anionic surfactants.

The nonionic surfactants that are suitable are ethoxylated fatty alcohols and ethoxylated fatty acids. Sulfonates and succinates may also be useful. Ethoxylates are produced by condensing ethylene oxide with a hydrocarbon having a reactive hydrogen atom in the presence of an acid or base catalyst. Such surfactants can be represented by the generic formula $RA(CH_2 CH_2O)_nH$ wherein R represents the hydrophobic moiety, A represents the group carrying the reactive hydrogen atom and n represents the group average number of ethylene oxide moieties. R typically contains about 8 to 22 carbon atoms, and n usually varies from about 2 to about 10, and preferably from about 2 to about 8 groups/mole, avg. The hydrophile/lipophile balance number (HLB) is preferably between about 3 to about 15. Preferred ethoxylated fatty alcohols nonionic surfactants include Neodol$^R$ 23-6.5 and Neodol$^R$ 25-3 (each available from Shell Chemical Co.; Parsippany, N.J.).

Anionic surfactants can be represented by the general formula RSOM wherein R represents a hydrocarbon selected from the group consisting of straight or branched alkyl radicals containing from about 8 to about 24 carbon atoms. M is a salt forming cation that typically is selected from the group consisting of sodium, potassium, ammonium and derivatives thereof. The preferred anionic surfactant is a simple salt such as for example, sodium laureth sulfate (available from Stepan Co., Northfield, Ill.).

The Enzymes:

Enyzmes that are useful in the present invention comprise proteases and alpha-amylases. The proteases are typically derived from bacterial sources and are preferably active in a pH range of about 4 to about 10 The preferred pH range is neutral to somewhat basic, from about a pH of 6.8 to about a pH of 9. A protease can break the peptide bonds of proteins found in blood and organic stains. This results in short chain molecules having free amino and carboxy groups, ionic groups that are more easily washed away with water and/or detergent. It is preferred that the protease be able to function at high temperatures (up to about 90 degrees C.) as well as at room temperature. An example of such a protease is Savinase$^R$ 16L which is available from Novo Nordisk Bio-Chem North America, Inc., Franklinton, N.C.

An amylase is an enzyme that catalyzes a reaction that breaks starch molecules into shorter chain molecules making the removal of the starch with water and/or detergent easier. Starches may enhance the adherence of proteins to fibers and hard surfaces. The preferred amylase is able to function at high temperatures (up to about 90 degrees C.) as well as at room temperature. Preferably, the amylase can function at a pH from about 6.8 to about 11.5 An example of an amylase is Termamyl$^R$ 300L which is available from Novo Nordisk BioChem North America, Inc., Franklinton, N.C.

Optionally, an enzyme that facilitates the breakdown of fats and oils into shorter chain molecules may be added to the spot remover. Such an enzyme is a lipase such as for example, Lipolase$^R$ which is available from Novo Nordisk BioChem North America, Inc., Franklinton, N.C. Fats and oils may enhance adherence of other organic molecules. By combining a lipase, a protease, and. optionally, an amylase in an aqueous detergent solution, the types of stains removed may be unexpectedly improved.

In the preferred blood and organic spot remover composition, at an amylase and a protease are present at a concentration of at least about 0. 1% w/w.

The Enzyme Activity Stabilizers:

Useful enzyme activity stabilizers include compounds that provide a source of free calcium in the solution such as for example calcium salts; alkyl or branched alcohols such as for example ethanol and isopropyl alcohol; alkanolamines such as for example triethanolamine and acids preferably organic acids; and mixtures of petroleum distillates. Up to 25% by weight of alcohol may be added to the spot remover. Preferably between 1–15% by weight of alcohol are added. Petroleum distillates such as for example mineral spirits may be added in amounts of up to 75% by weight with less than 25% being preferred.

The pH of the spot remover may be adjusted by adding an acid or a base to achieve the preferred pH which is from about 6.8 to 8.5. Alkanolamines such as for example triethanolamine, may. be added to make the solution more basic. Acids or salts of acids may be added to adjust the pH towards a lower pH. Useful carboxylic acid salt includes acetates and propionates. The preferred salt is sodium formate.

Unsaturated fatty acids may also be added such as for example oleic acid. Such fatty acids may serve a dual function by enhancing cleaning power and altering pH. To obtain the spot remover solution all ingredients are dissolved and mixed together. The final volume is adjusted with distilled water (DI).

The present invention is useful for cleaning up fresh and dried blood and organic stains and spots when packaged as a wiper, such as for example in a dentist's office. Alternatively, direct skin contact with the inventive composition and spot may be prevented by use of gloves by the user. The present invention may also find use as a germicide, such as when wiping up blood and organic stains. The inventive compositions also find use as pre-spotting compositions. For example, a spot or stain on a laboratory coat may be treated with the chosen inventive composition, then the laboratory coat is washed in the regular manner.

The present inventive composition(s) may be incorporated into prepackaged disposable wipers 10, for example such as illustrated in U.S. Pat. No. 4,998,984 (McClendon), the disclosure of which is incorporated herein by reference. The package may have an absorbent material wipe 12 attached to and enclosed in a metal foil package 14 provided with fold back flaps 16. The inventive composition selected from Formulae A or B is placed on the absorbent material prior to packaging. The fold-back flaps may be used to form a handle 18 for the wipe to clean up blood or spot an organic stain. After contacting the spot with the wipe and removing the spot, the flaps may be folded over the used wipe without the need for direct skin contact with the wipe. Alternate methods of packaging the invention composition which allow use without the need for direct skin contact with the blood or organic spot or stain or the inventive composition are contemplated. Additionally, the user may remove spots or stains with the invention compositions by protecting the skin through use of gloves.

The following examples illustrate the invention:

EXAMPLE 1

The following illustrate the compositions of the present invention. Preparation of the following Formulae is achieved by solubilizing, clarifying and mixing the components. All parts, percentages and ratios used herein are by weight unless otherwise specified.

| Formula A | | Formula B | |
|---|---|---|---|
| calcium chloride | 0.05% | Neodol<sup>R</sup> 25–3 | 10% |
| sodium formate | 2% | Neodol<sup>R</sup> 23–6.5 | 10% |
| triethanolamine | 1% | mineral spirits | 20% |
| ethanol | 5% | isopropanol | 12% |
| Neodol<sup>R</sup> 23–6.5 | 30% | triethanolamine | about 1.2% |
| Steol<sup>R</sup> CS-460 | 20% | oleic acid | about 2.3% |
| enzymes | 0.2–3% | calcium chloride | 0.05% |
| DI water | to 100% | sodium formate | 2% |
| | | enzymes | 0.2–3% |
| | | DI water | to 100% |

Enzymes: Savinase$^R$ 16L, Lipolase$^R$ 100L, and Termamyl$^R$ 300L.

EXAMPLE 2

The effectiveness of Formula A and Formula B at removing organic stains was tested with and without added enzymes on standardized swatches having the following compositions: I—blood, milk, carbon ink on 100% cotton (100%); II—blood, milk, carbon ink on polyester-cotton; III—cocoa and milk on 100% cotton; IV - maize starch and carbon ink on 100% cotton. Swatches I and II were observed for protease activity. Swatches III and IV were observed for amylase activity. Lipolase$^R$ 100L was observed to separate out of each of Formulae A and B.

On a weight/weight basis, equal amounts of each of Savinase$^R$ 16L, Lipolase$^R$ 100L, and Termamyl$^R$ 300L were tested in Formulae A and B at concentrations ranging from 0 to 0.5%. One milliliter aliquots of the respective Formulae were rubbed for 10 seconds into the stain on each of the standardized swatches. The standardized swatches were allowed to soak for 5 minutes and then were rinsed in tap water for 5 minutes. A refractometer (US Testing Co., Model 7243S) was used to provide reflectance measurements.

Figure 2:
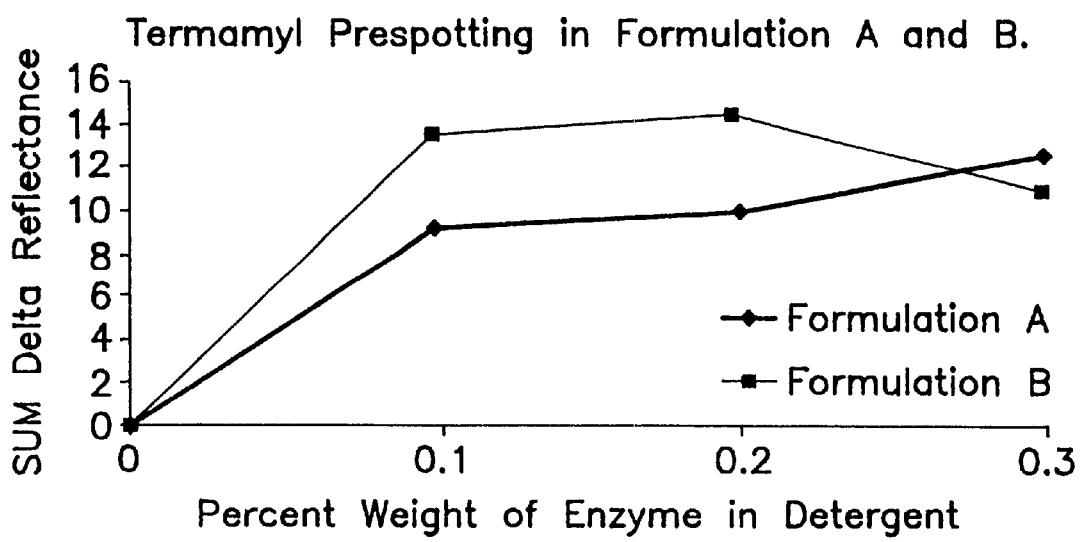
FIG. 2 illustrates the ability of Formula A and Formula B to remove stains having starch therein as measured by reflectance.

The results shown in FIG. 1 for protease activity and in FIG. 2 for protease/amylase activity, demonstrate that while the detergent composition alone was effective at removing organic stains, addition of the protease and the amylase greatly enhanced organic stain removal even at concentrations as low as 0. 1% w/w.

EXAMPLE 3

Figure 3A:
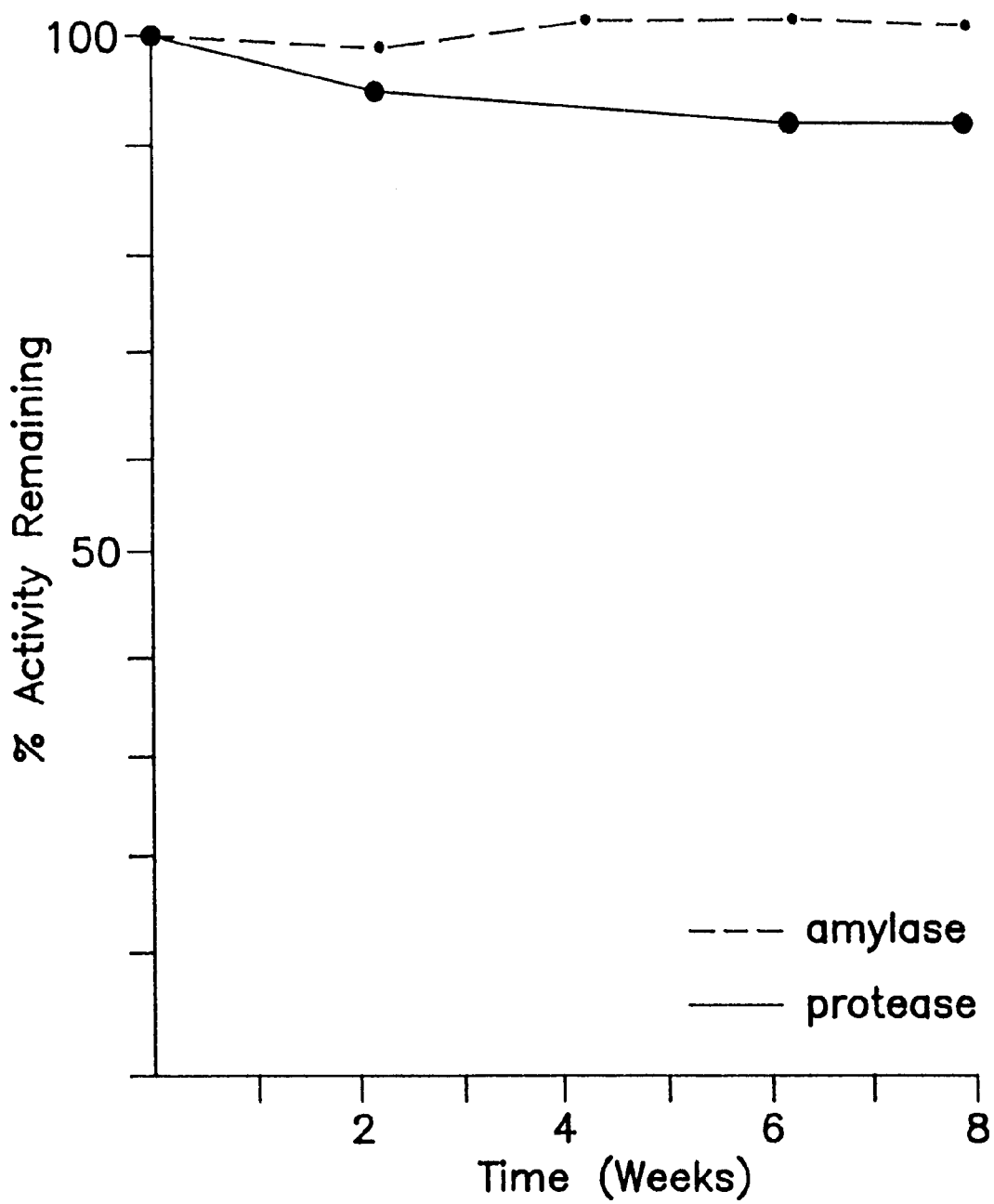
FIG. 3A illustrates the stability of Formula A with time as determined by the enzymatic activity therein.
Figure 3B:
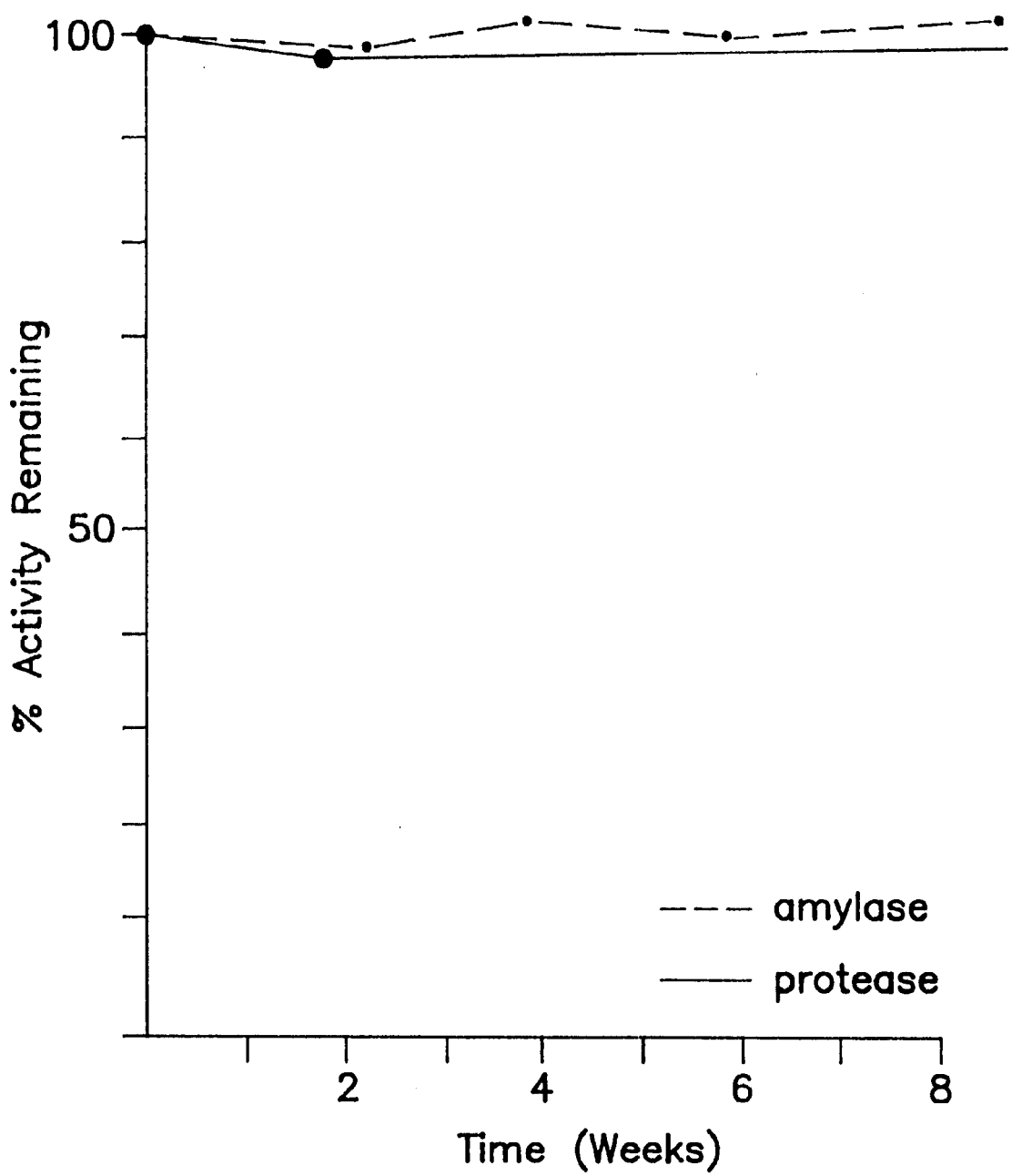
FIG. 3B illustrates the stability of Formula B with time as determined by the enzymatic activity therein.
Figure 4:
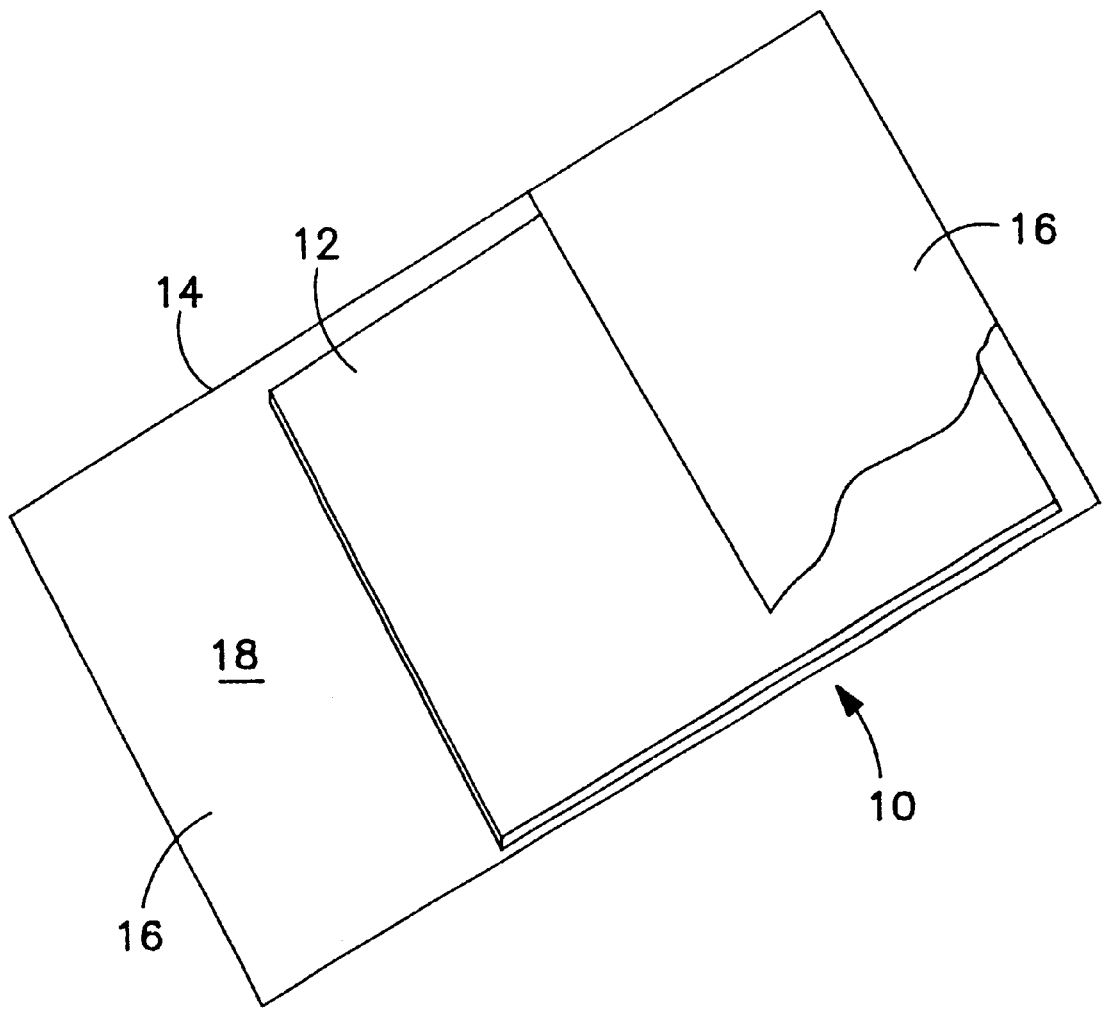
FIG. 4 is a pictorial representation of the prepackaged blood and organic stain remover of this invention.

Storage stability of Formulae A and B when 1% each of Savinase$^R$ 16L, Lipolase$^R$ 100L, and Termamyl$^R$ 300L were present in the aqueous detergent composition was determined using a standard accelerated stability test. An eight week incubation at an elevated temperature of 30 degrees C. was performed wherein enzymatic activity was determined at two week intervals. Each formulation was incubated in sealed glass vials in an incubation chamber (VWR Scientific Laboratories, Inc., Model #535). Enzymatic activity of the protease, amylase, and lipase was determined using a spectrophotometer (Carey, Inc., Model 3C) and protein or starch standards. Wash performance evaluation was performed using a terg-o-tometer (United States Testing Co., Inc.; 7243S). Results of the wash test were evaluated using a Hunter Labscan reflectometer (SN/13859). FIG. 3A illustrates protease stability with time in Formulae A and B. FIG. 3B illustrates amylase activity with time in Formulae A and B. It can be seen that both enzymes in both formulae retain greater than 90% activity with time.

The foregoing is considered only illustrative of the currently preferred embodiments of the invention presented herein. Since numerous modifications and changes will occur to those skilled in the art, it is not desired to limit the invention to the exact construction used to illustrate the various means comprising this invention.

What is claimed is:

1. A prepackaged blood and organic spot remover comprising a protease, an amylase, an enzyme stabilizing system, a detergent, and water, said prepackaged blood and organic spot remover being contained in a prepackaged disposable wiper having an absorbent material wipe attached thereto that is soaked with said blood and organic spot remover, said prepackaged disposable wiper being enclosed in a metal foil package provided with fold back flaps which can be used to form a handle for said prepackaged disposable wiper while cleaning up blood or an organic stain and which can be folded over said prepackaged disposable wiper once used.

2. A prepackaged blood and organic spot remover comprising an aqueous solution of 0.05% calcium chloride; 2% sodium formate; 1% triethanolamine; 5% ethanol; 30% linear primary alcohol ethoxylate selected from the group consisting of ethoxylated fatty alcohols and ethoxylated fatty acids represented by the generic formula RA(CH$_2$ CH$_{20}$O)$_n$H wherein R represents the hydrophobic moiety and has between 8 and 22 carbon atoms, A represents the group carrying the reactive hydrogen atom, and n represents the group average number of ethylene oxide moieties which is between 2 and 8; 20% sodium laureth sulfate; and an enzyme solution having a concentration of between 0.2% and 3% by weight wherein the enzymes present are protease, lipase, and alpha-amylase; said prepackaged blood and organic spot remover being contained in a prepackaged disposable wiper having an absorbent material wipe attached thereto that is soaked with said blood and organic spot remover, said prepackaged disposable wiper being enclosed in a metal foil package provided with fold back flaps which can be used to form a handle for said prepackaged disposable wiper while cleaning up blood or an organic stain and which can be folded over said prepackaged disposable wiper once used.

3. A prepackaged blood and organic spot remover comprising an aqueous solution of 20% linear alcohol ethoxylate selected from the group consisting of ethoxylated fatty alcohols and ethoxylated fatty acids represented by the generic formula RA(CH$_2$ CH$_{20}$O)$_n$H wherein R represents the hydrophobic moiety and has between 8 and 22 carbon atoms, A represents the group carrying the reactive hydrogen atom, and n represents the group average number of ethylene oxide moieties which is between 2 and 8; 20% mineral spirits; 12% isopropanol; about 1.2% triethanolamine; 2.3% oleic acid; 0.05% calcium chloride; 2% sodium formate; and an enzyme solution having a concentration of between 0.2% and 3% by weight wherein the enzymes present are protease, lipase, and alpha-amylase; said prepackaged blood and organic spot remover being contained in a prepackaged disposable wiper having an absorbent material wipe attached thereto that is soaked with said blood and organic spot remover, said prepackaged disposable wiper being enclosed in a metal foil package provided with fold back flaps which can be used to form a handle for said prepackaged disposable wiper while cleaning up blood or an organic stain and which can be folded over said prepackaged disposable wiper once used.

4. The blood and organic spot remover of claim 1 wherein said blood and organic spot remover has germicidal properties.

5. The blood and organic spot remover of claim 1 wherein said blood and organic spot remover is biodegradable.

6. The blood and organic spot remover of claim 1 wherein the activity range of the protease is between pH 6.8 and 9.

7. The blood and organic spot remover of claim 1 wherein the protease will function at temperatures of about 90 degrees C.

8. The blood and organic spot remover of claim 1 wherein the activity range of the amylase is between pH 6.8 and 11.5.

9. The blood and organic spot remover of claim 1 wherein the amylase will function at temperatures of about 90 degrees C.

10. The blood and organic spot remover of claim 1 wherein lipase is included.

11. The blood and organic spot remover of claim 1 wherein the combined concentration of the protease and the amylase is 0.1% by weight.

12. The blood and organic spot remover of claim 1 wherein the activity of the protease and the amylase is between 80% and 90% after 8 weeks of storage.

13. The blood and organic spot remover of claim 1 wherein the enzyme stabilizing system includes an alkanolamine, a calcium salt, and an alcohol.

14. The blood and organic spot remover of claim 13 wherein the alkanolamine is triethanolamine.

15. The blood and organic spot remover of claim 13 wherein the alcohol is selected from the group consisting of alkyl alcohols and branched alcohols.

16. The blood and organic spot remover of claim 15 wherein the alkyl alcohol is selected from the group consisting of ethanol and isopropyl alcohol.

17. The blood and organic spot remover of claim 13 wherein the alcohol is present at concentrations of up to 25% by weight.

18. The blood and organic spot remover of claim 1 wherein the enzyme stabilizing system further includes a petroleum distillate.

19. The blood and organic spot remover of claim 18 wherein the petroleum distillate is mineral spirits.

20. The blood and organic spot remover of claim 18 wherein the petroleum distillate is present at concentrations of up to 75% by weight.

21. The blood and organic spot remover of claim 1 wherein the detergent is nonionic.

22. The blood and organic spot remover of claim 21 wherein the hydrophile/lipophile balance number of the nonionic detergent is between about 3 and about 15.

23. The blood and organic spot remover of claim 21 wherein the nonionic detergent is selected from the group consisting of ethoxylated fatty alcohols and ethoxylated fatty acids represented by the generic formula $RA(CH_2CH_2O)_nH$ wherein R represents the hydrophobic moiety and has between 8 and 22 carbon atoms, A represents the group carrying the reactive hydrogen atom, and n represents the group average number of ethylene oxide moieties which is between 2 and 8.

24. The blood and organic spot remover of claim 1 wherein the detergent is anionic.

25. The blood and organic spot remover of claim 24 wherein the anionic detergent is represented by the general formula RSOM wherein R represents a hydrocarbon selected from the group consisting of straight or branched alkyl radicals containing from about 8 to about 24 carbon atoms, M is a salt forming cation which is selected from the group consisting of sodium, potassium, ammonium and derivatives thereof.

26. The blood and organic spot remover of claim 24 wherein the anionic detergent is sodium laureth sulfate.

27. The blood and organic spot remover of claim 1 wherein the water comprises between 40% and 50% of total weight.

* * * * *

UNITED STATES PATENT AND TRADEMARK OFFICE
CERTIFICATE OF CORRECTION

PATENT NO. : 6,420,332 B1
DATED : July 16, 2002
INVENTOR(S) : Joseph J. Simpson

It is certified that error appears in the above-identified patent and that said Letters Patent is hereby corrected as shown below:

Column 6,
Lines 23 and 44, "$RA(CH_2\ CH_{20}O)_nH$" should read -- $RA(CH_2\ CH_2O)_nH$ --.

Signed and Sealed this

Seventeenth Day of December, 2002

JAMES E. ROGAN
*Director of the United States Patent and Trademark Office*